United States Patent [19]

Yamada et al.

[11] Patent Number: 5,413,991
[45] Date of Patent: May 9, 1995

[54] ALLOSAMIDIN COMPOUNDS

[75] Inventors: Yasuhiro Yamada, Ikeda; Shohei Sakuda, Takatsuki; Seiji Takayama, Kasawaki, all of Japan

[73] Assignee: Ajinomoto Co., Inc., Tokyo, Japan

[21] Appl. No.: 830,353

[22] Filed: Jan. 31, 1992

[30] Foreign Application Priority Data

Jan. 31, 1991 [JP] Japan .................................. 3-011028

[51] Int. Cl.[6] .............................................. A61K 31/70
[52] U.S. Cl. ........................................ 514/27; 536/17.4; 514/53
[58] Field of Search ..................... 536/17.4; 514/27, 53

[56] References Cited

U.S. PATENT DOCUMENTS 5,070,191 12/1991 Yamada et al. ...................... 536/22

FOREIGN PATENT DOCUMENTS 0395106 10/1990 European Pat. Off. .

OTHER PUBLICATIONS

Journal of Antibiotics, vol. 44, No. 7, pp. 716–722, Jul. 1991, Y. Nishimoto, et al., "Isolation and Characterization of New Allosamidins".
Agricultural and Biological Chemistry, vol. 54, No. 5, pp. 1333–1335, Apr. 1990, S. Sakuda, et al., "Effects of Demethylallosamidin, a Potent Yeast Chitinase Inhibitor, on the Cell Division of Yeast".
Agricultural and Biological Chemistry, vol. 53, No. 10, pp. 2825–2826, Oct. 1989, A. Isogai, et al., "Structure of Demethylallosamidin as an Insect Chitinase Inhibitor".
Agricultural and Biological Chemistry, vol. 51, No. 12, pp. 3251–3259, Dec. 1987, S. Sakuda, et al., "Structures of Allosamidins, Novel Insect Chitinase Inhibitors, Produced by Actinomycetes".
Patent Abstracts of Japan, vol. 12, No. 70, (C–479) (2917), Mar. 4, 1988, & JP-A-62-207-294, Sep. 11, 1987, A. Suzuki, et al., "Novel Substance Allosamidine and Production and Use Thereof".
Sakuda et al, J. of Antibiotics vol. 40, pp. 296–300 (1987).
Sakuda et al, Chemical Abstract, vol. 109 (1988) No. 69316u.
Nishimoto et al, Chemical Abstracts, vol. 115 (1991) No. 154612f.

*Primary Examiner*—John W. Rollins
*Assistant Examiner*—Elli Peselev
*Attorney, Agent, or Firm*—Oblon, Spivak, McClelland, Maier, & Neustadt

[57] ABSTRACT

Novel allosamidin compounds, AJI9463A, AJI9463B and AJI9463C, represented by the following structural formula (1):

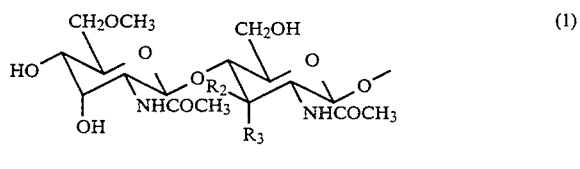

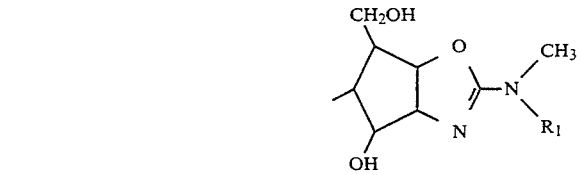

wherein $R_1$ and $R_2$ are hydrogen and $R_3$ is hydroxy (AJI9463A); $R_1$ and $R_3$ are hydrogen and $R_2$ is hydroxy (AJI9463B); and $R_1$ is methyl, $R_2$ is hydroxy and $R_3$ is hydrogen (AJI9463C), exhibit extremely potent inhibitory activity against chitinases from a number of sources, particularly from *Candida albicans*, and can be utilized as potent antifungal agents and chitinase inhibitors. Pseudo disaccharide compounds, obtained by partial hydrolysis of these compounds with an acid, also show potent inhibitory activity against chitinase, and can be utilized as antifungal agents and chitinase inhibitors.

8 Claims, 4 Drawing Sheets

ALLOSAMIDIN COMPOUNDS

BACKGROUND OF THE INVENTION

1. Field of the Invention

The present invention relates to novel allosamidin compounds which are useful in the fields of agricultural chemicals, animal and human drugs, etc., compositions containing the novel allosamidin compounds, and processes for the production of the novel allosamidin compounds.

2. Discussion of the Background

Chitin is the main component of cell walls. During division and proliferation of fungi, the synthesis of chitin is well-balanced with its decomposition. Chitin is also the principal component found in the exoskeletons of insects. The synthesis and decomposition of chitin are also elaborately controlled in the process where insects cast the skin and grow.

Chitinase is the major enzyme which participates in the metabolism of chitin. Inhibitors of this enzyme represent a new class of antifungal agents and/or insect growth control agents.

Heretofore, three chitinase inhibitors were known: allosamidin (S. Sakuda et al., *J. Antibiotics*, vol. 40, pp. 296–300, 1987), methylallosamidin (S. Sakuda et al., *Preprint of 28th Discussions and Lectures on Natural Organic Compounds*, p. 70, 1986) and demethylallosamidin (S. Sakuda et al., *Agric. Biol. Chem.*, vol. 54, pp. 1333–1335, 1990).

Among them, allosamidin and methylallosamidin are inhibitors of silkworm-derived chitinase. These compounds also strongly inhibit the endo-type chitinase of insects, but show a weak inhibitory activity against fungi-derived chitinase. Demethylallosamidin shows a potent inhibitory activity against chitinase from baker's yeast (*Saccharomyces cerevisiae*), but its inhibitory activity against the chitinase of pathogenic fungi such as *Candida albicans* is insufficient for its use as an anti-fungal agent. Thus, a more potent and/or broader-spectrum chitinase inhibitor is desired.

The three substances described above all have a pseudo trisaccharide structure, composed of two 2-amino-2-deoxy-D-allose (or N-acetylallosamine) molecules and one allosamizoline (or demethylallosamizoline) molecule. These compounds represent the first time N-acetylallosamine has been found as a constituent in a natural product. To date, no other natural source of allosamidin has been found. Accordingly, there is no abundant supply of these compounds. Furthermore, no industrially useful synthesis of allosamine or compound containing allosamine is known.

To meet the needs for (1) a more potent chitinase inhibitor, (2) a chitinase inhibitor which exhibits inhibitory activity against a broad spectrum of chitinases (that is, chitinases from a variety of sources), and (3) an industrially useful synthesis of allosamine and/or compounds containing allosamine, the present Inventors have discovered and investigated novel allosamidin compounds, AJI9463A, AJI9463B and AJI9463C, produced by microorganisms belonging to the genus Streptomyces, and partially-hydrolyzed disaccharides thereof. These compounds have been shown to have potent inhibitory activity against chitinase from a number of sources, and have anti-fungal activity against pathogenic fungi.

SUMMARY OF THE INVENTION

Accordingly, one object of the present invention is to provide compounds having potent chitinase inhibitory activity.

A further object of the present invention is to provide compounds having potent anti-fungal activity.

A further object of the present invention is to provide compounds having insecticidal activity.

A further object of the present invention is to provide compositions having potent chitinase inhibitory activity.

A further object of the present invention is to provide compositions having potent anti-fungal and/or insecticidal activity.

A further object of the present invention is to provide industrially useful processes for preparing chitinase inhibitors.

A further object of the present invention is to provide industrially useful processes for preparing anti-fungal and/or insecticidal agents.

These and other objects will become apparent during the following detailed description of the present invention, wherein novel allosamidins compounds AJI9463A, AJI9463B and AJI9463C, represented by the following chemical structure (1):

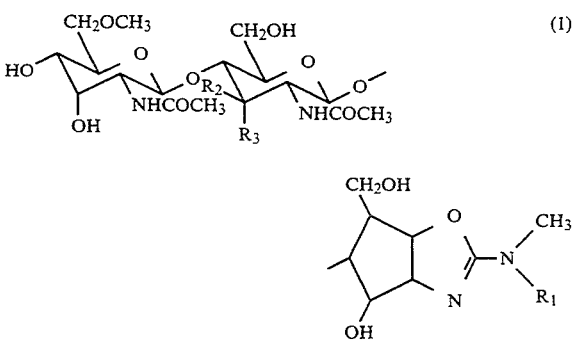

which are prepared by culturing in a suitable medium bacteria capable of producing these compounds and isolating the compounds from the culture; and the partially hydrolyzed disaccharides of allosamidin compounds AJI9463A, AJI9463B and AJI9463C, represented by the following chemical structure (2):

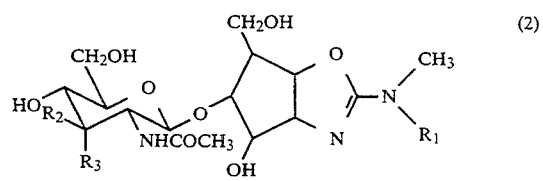

wherein for both chemical structures (1) and (2), $R_1$ and $R_2$ are hydrogen and $R_3$ is hydroxy; $R_1$ and $R_3$ are hydrogen and $R_2$ is hydroxy; or $R_1$ is methyl, $R_2$ is hydroxy and $R_3$ is hydrogen, are shown to have potent inhibitory activity of chitinases from a number of sources, such as those derived from *Candida albicans*, baker's yeast and Trichioderma, and inhibitory activity against the growth of pathogenic fungi, such as *Candida albicans*.

DETAILED DESCRIPTION OF THE PREFERRED EMBODIMENTS

Figure 1:
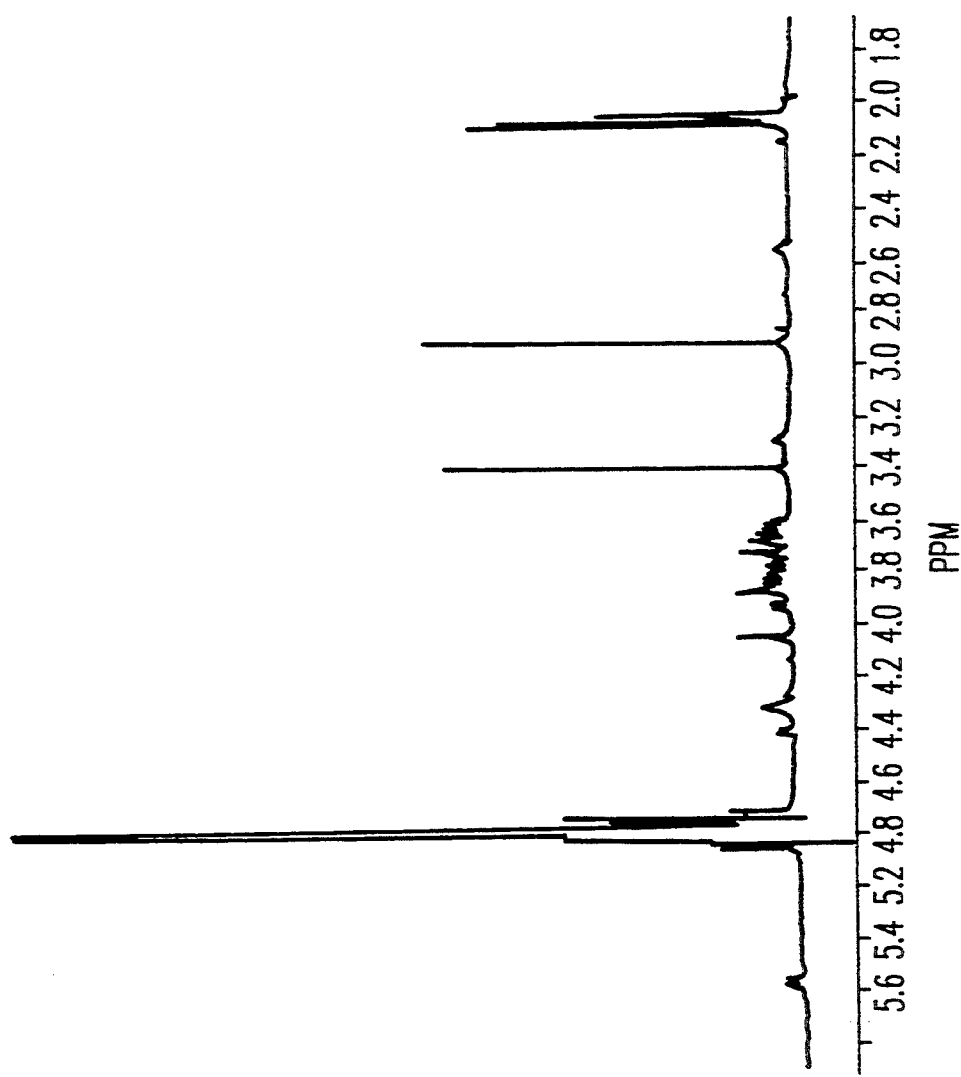
FIG. 1 shows the proton nuclear magnetic resonance spectrum of AJI9463A.

The present Inventors have discovered that novel allosamidin compounds AJI9463A, AJI9463B and AJI9463C, represented by the following chemical structure (1), produced by certain allosamidin-producing bacteria, exhibit extremely potent inhibitory activity against a number of chitinases from various sources, and also inhibit the growth of pathogenic fungi:

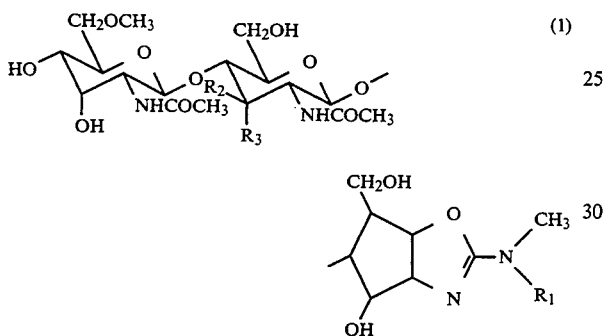

In AJI9463A, $R_1$ and $R_2$ are hydrogen and $R_3$ is hydroxy; in AJI9463B, $R_1$ and $R_3$ are hydrogen and $R_2$ is hydroxy; and in AJI9463C, $R_1$ is methyl, $R_2$ is hydroxy and $R_3$ is hydrogen. These compounds are produced by, for example, bacteria belonging to the genus Streptomyces, specifically the strains Streptomyces sp. AJ9463 (FERM BP-2801) or Streptomyces sp. AJ9472 (FERM BP-3705). Cultures of Streptomyces sp. AJ9463 and Streptomyces sp. AJ9472 have been deposited with the Fermentation Research Institute, Agency of Industrial Science and Technology (1-3, Higashi, 1-chome, Tsukuba-shi, Ibaraki-ken 305, Japan) under the deposit numbers FERM BP-2801 and FERM BP-3705, respectively.

The present Inventors have also discovered that partially hydrolyzed disaccharides of the allosamidin compounds AJI9463A, AJI9463B and AJI9463C, represented by the following chemical structure (2), also exhibit extremely potent inhibitory activity against fungi-derived chitinase, and also inhibit the growth of pathogenic fungi:

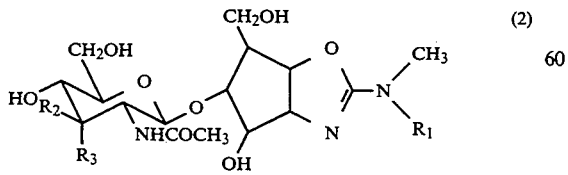

wherein $R_1$ represents hydrogen or methyl; when $R_1$ is hydrogen, $R_2$ is hydrogen and $R_3$ is hydroxy (the partially hydrolyzed disaccharide of AJI9463A), or $R_2$ is hydroxy and $R_3$ is hydrogen (the partially hydrolyzed disaccharide of AJI9463B); and when $R_1$ is methyl, $R_2$ is hydroxy and $R_3$ is hydrogen (the partially hydrolyzed disaccharide of AJI9463C).

The bacteriological properties of Streptomyces sp. AJ9463 (FERM BP-2801) are as follows:

1. Morphological characteristics

Under microscopic observation, substrate mycelium is branched on various nutrient agar media, and grows well to form well-extended aerial mycelium. No verticillate branching is noted. The shape of spore chains is mostly straight or loose loop. Mature spores are oval, and have a size of approximately $1 \times (1.5-2)$ μm. The surface is smooth but wrinkled. Spores form chains of 10 to 50 and the boundary between spores is somewhat unclear. Sporangia, sclerotic granules, motile spores, etc. are not observed.

2. Growth conditions in various media

Color hue indications in various media shown below are in accordance with the color standard defined by the Japanese Color Research Institute.

(1) Sucrose nitrate agar medium

Moderate growth. Almost colorless substrate mycelium, on which light grey aerial mycelia are formed. Neither remarkable color nor soluble pigment is noted on the back surface.

(2) Glucose asparagine agar medium

Good growth. Aerial mycelia are little noted on light brown substrate mycelium. Neither remarkable color nor soluble pigment is noted on the back surface.

(3) Glycerine asparagine agar medium (ISP5 medium)

Moderate or poor growth. White or grey aerial mycelia are slightly formed on almost colorless substrate mycelium. Neither remarkable color nor soluble pigment is noted on the back surface.

(4) Starch agar medium (ISP4 medium)

Good growth. White, grey or black aerial mycelia are scatteringly formed on grayish red brown substrate mycelium. Neither remarkable color nor soluble pigment is noted on the back surface.

(5) Tyrosine agar medium (ISP7 medium)

Moderate or poor growth. White to grey aerial mycelia are slightly formed on almost colorless substrate mycelium. Neither remarkable color nor soluble pigment is noted on the back surface.

(6) Nutrient agar medium

Good growth. Grey aerial mycelia are abundantly formed on light yellowish brown substrate mycelium. Neither remarkable color nor soluble pigment is noted on the back surface.

(7) Yeast maltose agar medium (ISP2 medium)

Good growth. Grey aerial mycelia are scatteringly formed on light brown substrate mycelium. Neither remarkable color nor soluble pigment is noted on the back surface, but back surface is slightly grayish yellow-brown.

(8) Oatmeal agar medium (ISP3 medium)

Good growth. Grey aerial mycelia are abundantly formed on grayish brown substrate mycelium. Neither remarkable color nor soluble pigment is noted on the back surface, but back surface is slightly grayish brown.

3. Physiological characteristics (1) Growth temperature range: 10°–42° C.

(2) Liquefaction of gelatin:

Liquefaction of gelatin was noted at both 20° C. and 27° C. when cultured in glucose peptone gelatin medium.

(3) Hydrolysis of starch:
Positive on starch agar medium (ISP4 medium)

(4) Solidification and peptonization of skimmed milk:
Strong solidification is noted at 37° C., but no peptonization is observed. At 27° C., no solidification is observed, but strong peptonization is noted.

(5) Formation of melanine-like pigment:
Negative on tyrosine agar medium (ISP7 medium)

(6) Assimilation of carbon sources (Pridham-Gotlieb medium):
good assimilation:
D-glucose, D-xylose, L-rammnose, raffinose
moderate assimilation:
D-fructose, sucrose
no assimilation:
L-arabinose, inositol, D-mannitol 2,6-Diaminopimelic acid contained in the cell wall was LL-type.

From the properties described above, it was determined that the strain AJ9463 was *Streptomyces sp.*

The bacteriological properties of *Streptomyces sp.* AJ9472 (FERM BP-3705) are as follows:

1. Morhpological characteristics
Under microscopic observation, substrate mycelia are branched on various nutrient agar media, and grow well to form well-extended aerial mycelia. No verticillate branching is noted. The shape of spore chains is mostly straight or loose loop, and spore chains are, in part, branched. Mature spores are oval or spherical, and have a size of approximately (0.5–0.7) to 2 μm. The surface is smooth. Spores form chains of approximately 20 to 100, and the boundary between spores is somewhat clear. Sporangia, motile spores, etc. are not observed.

2. Growth conditions in various media
Color hue indications in various media shown below are in accordance with the color standard defined by the Japanese Color Research Institute.

(1) Sucrose nitrate agar medium
Poor growth. White to brownish grey aerial mycelia are slightly formed on almost colorless substrate mycelium. Neither remarkable color nor soluble pigment is noted on the back surface.

(2) Glucose asparagine agar medium
Moderate growth. White to brownish white aerial mycelia are formed well on almost colorless substrate mycelium. Neither remarkable color nor soluble pigment is noted on the back surface.

(3) Glycerine asparagine agar medium (ISP5 medium)
Moderate or poor growth. White or brownish white aerial mycelia are slightly formed on almost colorless substrate mycelium. Neither remarkable color nor soluble pigment is noted on the back surface.

(4) Starch agar medium (ISP4 medium)
Moderate growth. White or brownish white aerial mycelia are abundantly formed on almost colorless substrate mycelium. Neither remarkable color nor soluble pigment is noted on the back surface.

(5) Tyrosine agar medium (ISP7 medium)
Good or moderate growth. White to brownish white aerial mycelia are moderately formed on almost colorless or yellowish grey substrate mycelium. Neither remarkable color nor soluble pigment is noted on the back surface.

(6) Nutrient agar medium
Good growth. White aerial mycelia are abundantly formed on light yellowish brown substrate mycelium. Neither remarkable color nor soluble pigment is noted on the back surface, but back surface is somewhat light yellowish brown.

(7) Yeast maltose agar medium (ISP2 medium)
Good growth. Brownish white aerial mycelia are abundantly formed on brown substrate mycelium. A light brown color is noted on the back surface, and soluble pigment is light brown.

(8) Oatmeal agar medium (ISP3 medium)
Good growth. White or brownish white aerial mycelia are abundantly formed on almost colorless or yellowish grey substrate mycelium. Neither remarkable color nor soluble pigment is noted on the back surface.

3. Physiological characteristics
(1) Growth temperature range: 10°–42° C.
(2) Liquefaction of gelatin:
Liquefaction of gelatin was noted at both 20° C. and 27° C. when cultured in glucose peptone gelatin medium.
(3) Hydrolysis of starch:
Negative on starch agar medium (ISP4 medium)
(4) Solidification and peptonization of skimmed milk:
Solidification is negative, but peptonization is positive at 27° C. Solidification and peptonization are both negative at 37° C.
(5) Formation of melanine-like pigment:
Negative on tyrosine agar medium (ISP7 medium)
(6) Assimilation of carbon sources (Pridham-Gotlieb medium: ISP9 medium)
good assimilation:
D-glucose, L-rammnose
moderate assimilation:
D-xylose, raffinose
no assimilation:
L-arabinose, D-fructose, sucrose, inositol, D-mannitol 2,6-Diaminopimelic acid contained in the cell wall was LL-type.

From the properties described above, it was determined that the strain AJ9472 was *Streptomyces sp.*

Culture methods are performed in a manner conventionally used for culture of ordinary microorganisms, but deep tank culture using a liquid medium is generally advantageous. The medium used for culture may be any medium which contains nutrient sources the producing bacteria can assimilate. For example, suitable carbon sources include glucose, fructose, starch, dextrin, etc., and suitable nitrogen sources include meat extract, casein, gluten, yeast extract, soybean powder, corn steep liquor, urea, ammonium sulfate, ammonium phosphate, etc. In addition, inorganic salts such as sodium hydrogen phosphate, magnesium sulfate, calcium carbonate, etc., may be included, if necessary and/or if desired. Where foaming is vigorous during culture, small quantities of defoaming agents such as silicone compounds, higher alcohols, vegetable oils, etc., may also be added.

The culture is carried out preferably at 20° to 38° C., most preferably at about 27° C. Suitable lengths of time for the culture may be from about 1 to about 10 days, but may vary appropriately depending upon culture conditions.

AJI9463A, AJI9463B and AJI9463C accumulate mainly in the cells during culture of the microorganisms. Therefore, generally, the cells are separated from the culture by means of centrifugation, filtration, etc., and the compounds are isolated and purified from the cells using conventional means such as those used for isolation of antibiotics from cells. Specifically, conventional means for purification, such as solvent extraction with lower alcohols (for example, methanol, ethanol, n-butanol, etc.); adsorption column chromatography using silica gel, diatomaceous earth, Avicel, alumina, etc.; gel filtration using TOYOPEARL HW40 (carrier for gel filtration manufactured by TOSO Co., Ltd.), etc.; various ion exchange chromatographies and HPLC; and other purification means, such as countercurrent distribution, crystallization, recrystallization, etc., are used successively or in appropriate combination to isolate and purify AJI9463A, AJI9463B and AJI9463C from the cultured cells.

The resulting isolated and purified allosamidin compounds (AJI9463A, AJI9463B and AJI9463C) have the following physicochemical properties.

(1) AJI9463A
 (a) External appearance: white powder
 (b) Molecular weight: 622 (FAB MS: m/z 623 $(M+H)^+$, glycerol matrix)
 (c) Molecular formula: $C_{25}H_{42}N_4O_{14}$
 (d) UV absorption spectrum: terminal absorption in 0.1 N acetic acid
 (e) $^1$H-nuclear magnetic resonance spectrum (600 MHz, in heavy water ($D_2O$) containing 3% $CD_3COOD$ [acetic acid-$d_4$]): see FIG. 1
 (f) $^{13}$C-nuclear magnetic resonance spectrum (150 MHz, $D_2O$ containing 3% $CD_3COOD$) $\delta=174.6$ (q), 174.3 (q), 162.4 (q), 101.2 (CH), 99.9 (CH), 87.6 (CH), 85.5 (CH), 80.8 (CH), 77.5 (CH), 73.2 (CH), 72.7 (CH), 72.0 (CH), 70.6 (CH), 69.7 (CH), 67.1 (CH), 65.0 (CH), 61.5 (CH2), 60.0 (CH2), 59.3 (CH3), 53.4 (CH), 53.2 (CH), 52.3 (CH), 29.0 (CH3), 22.6 (CH3), 22.6 (CH3). (It is assumed that this compound takes a plurality of conformations in the solvent, and therefore, shows a plurality of minor signals caused by the various conformations.)

Figure 2:
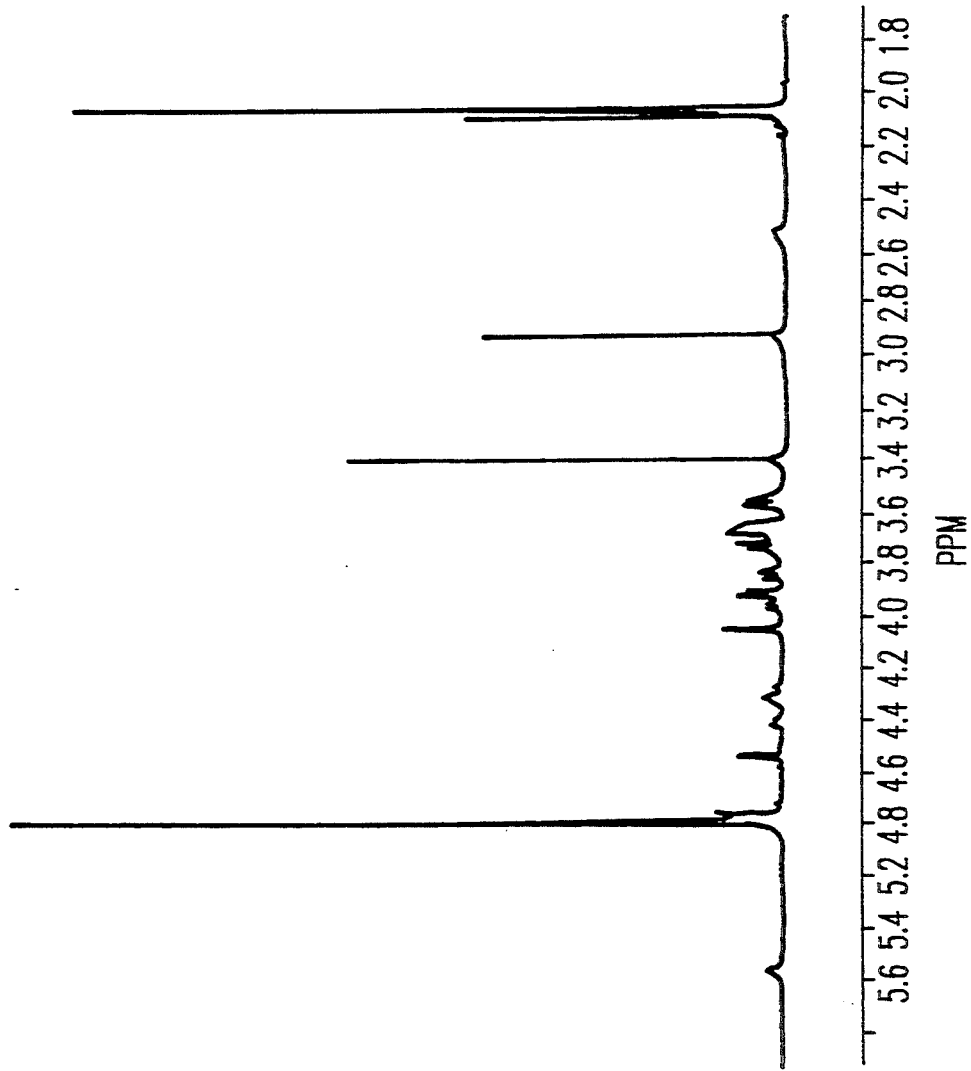
FIG. 2 shows the proton nuclear magnetic resonance spectrum of AJI9463B.

(2) AJI9463B
 (a) External appearance: white powder
 (b) Molecular weight: 622 (FAB MS: m/z 623 $(M+H)^+$, glycerol matrix)
 (c) Molecular formula: $C_{25}H_{42}N_4O_{14}$
 (d) UV absorption spectrum: terminal absorption in 0.1 N acetic acid
 (e) $^1$H-nuclear magnetic resonance spectrum (600 MHz, $D_2O$ containing 3% $CD_3COOD$): see FIG. 2
 (f) $^{13}$C-nuclear magnetic resonance spectrum (150 MHz, $D_2O$ containing 3% $CD_3COOD$): $\delta=175.0$ (q), 174.5 (q), 162.4 (q), 101.9 (CH), 100.6 (CH), 87.4 (CH), 85.5 (CH), 80.9 (CH), 80.7 (CH), 75.0 (CH), 73.2 (CH), 72.9 (CH), 72.1 (CH2), 70.6 (CH), 67.3 (CH), 64.9 (CH), 60.9 (CH2), 60.0 (CH2), 59.3 (CH3), 55.5 (CH), 53.3 (CH), 52.2 (CH), 29.0 (CH3), 22.8 (CH3), 22.6 (CH3). (It is assumed that this compound takes a plurality of conformations in the solvent, and shows a plurality of minor signals other than those described above.)

Figure 3:
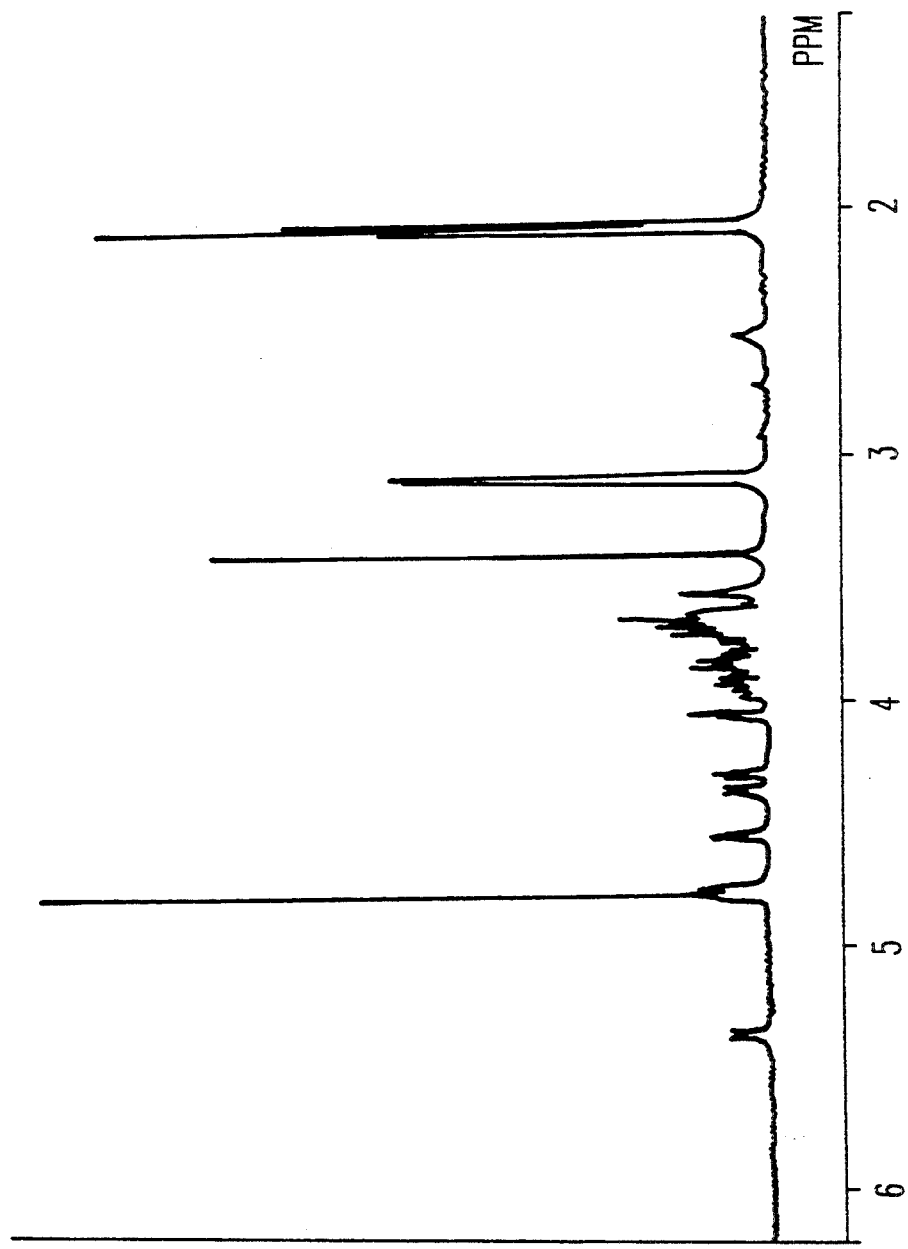
FIG. 3 shows the proton nuclear magnetic resonance spectrum of AJI9463C.

(3) AJI9463C
 (a) External appearance: white powder
 (b) Molecular weight: 636 (FAB MS: m/z 637 $(M+H)^+$, glycerol matrix)
 (c) Molecular formula: $C_{26}H_{44}N_4O_{14}$
 (d) UV absorption spectrum: terminal absorption in 0.1 N acetic acid
 (e) $^1$H-nuclear magnetic resonance spectrum (400 MHz, $D_2O$ containing 0.5% $CD_3COOD$): see FIG. 3
 (f) $^{13}$C-nuclear magnetic resonance spectrum (100 MHz, $D_2O$ containing 0.5% $CD_3COOD$): $\delta=175.1$ (q), 174.5 (q), 161.2 (q), 102.4 (CH), 100.6 (CH), 87.1 (CH), 85.5 (CH), 81.0 (CH), 80.9 (CH), 75.0 (CH), 73.1 (CH), 72.9 (CH), 72.1 (CH2), 70.6 (CH), 67.3 (CH), 64.9 (CH), 60.9 (CH2), 59.7 (CH2), 59.3 (CH3), 55.6 (CH), 53.3 (CH), 51.9 (CH), 38.0 (CH3), 22.8 (CH3), 22.6 (CH3).

The structural formulae of these compounds are shown above in chemical structure (1). AJI9463A is a novel compound in which the hydroxy group at the 6-position of the terminal allosamine ring is methylated, as in methylallosamidin. Against chitinase derived from Candida albicans, this compound shows the most potent inhibitory activity of any known compound.

Unlike known allosamidins, AJI9463B and AJI9463C are novel compounds where one of the two N-acetylallosamines is replaced by N-acetylglucosamine. The inhibitory activity of these compounds against chitinase derived from Candida albicans is superior to that of allosamidin and methylallosamidin. N-acetylallosamidin is an acetylated amino sugar present abundantly in the natural world, and provides an abundant source of N-acetylallosamine for chemical synthesis of the new compounds AJI9463B and AJI9463C. This is advantageous for producing the allosamidins on an industrial scale.

The compounds represented by chemical structural formula (1) can also be subjected to partial hydrolysis under mild conditions (e.g., warming to a temperature of 40°–100°, preferably 60°–80° C.), which can be catalyzed by acids such as dilute organic (e.g. substituted or unsubstituted lower alkanoic acids, such as acetic acid, chloroacetic acid, trifluoroacetic acid, etc.) or mineral acid (preferably dilute hydrochloric acid), whereby the present partially hydrolyzed allosamidin compounds represented by the following chemical structural formula (2) are provided:

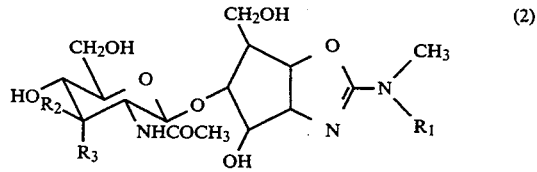

(2)

wherein $R_1$ represents hydrogen or methyl; when $R_1$ is hydrogen, $R_2$ is hydrogen and $R_3$ is hydroxy (the partially hydrolyzed disaccharide of AJI9463A), or $R_2$ is hydroxy and $R_3$ is hydrogen (the partially hydrolyzed disaccharide of AJI9463B); and when $R_1$ is methyl, $R_2$ is hydroxy and $R_3$ is hydrogen (the partially hydrolyzed disaccharide of AJI9463C). The substituents $R^1$, $R^2$ and $R^3$ of the partially hydrolyzed disaccharides are the same substituents as in the corresponding allosamidin compounds.

Isolation and purification of the partially hydrolyzed disaccharides may be effected by appropriately combining the means described above for isolation and purification of AJI9463A, AJI9463B and AJI9463C.

These compounds represented by chemical structural formula (2) are pseudo disaccharides. These compounds show an inhibitory activity against chitinase derived from *Candida albicans* comparable to the pseudo trisaccharides prior to the partial hydrolysis. In particular, the compounds of N-acetylglucosamine type in which $R_2$ is hydroxy and $R_3$ is hydrogen are easily synthesized chemically. Therefore, from an industrial viewpoint, the N-acetylglucosamine-type compounds are considered to be important.

The partially hydrolyzed disaccharides may be chemically synthesized by the following procedure. Allosamizoline is synthesized by a known method; e.g., the method of Trost et al (*J. Amer. Chem. Soc.*, vol. 112, pp. 1261-1263 (1990)). N-methylallosamizoline can be prepared from allosamizoline by conventional methods for N-methylation of amines. After protecting the hydroxy groups at the 6- and 3-positions of allosamizoline or N-methylallosamizoline, either with a protective group (such as benzoyl) or by formation of an acetal (such as an isopropylidene acetal), a sugar such as N-acetylglucosamine or N-acetylallosamine (or appropriate derivatives, isomers or analogs thereof) may then be bound to the hydroxy group at the 4-position of allosamizoline. Preferably, N-acetylglucosamine is used directly in the synthesis of AJI9463B and AJI9463C, and N-acetylallosamine is reacted directly to produce AJI9463A.

As stated above, the allosamidin compounds represented by either chemical structural formula (1) or (2) show a potent inhibitory activity against chitinase derived from *Candida albicans*. These compounds also cause morphological abnormalities in and affect the growth progress of various fungi, including the genus Candida and the genus Fusarium.

On the other hand, these compounds have low cytotoxicity, and show no growth arrest on mouse ascites breast cancer cells or human leukemia cells, even at a concentration of 1 mg/ml.

Therefore, compositions incorporating any of these compounds may be utilized as, for example, antifungal agents or insecticidal agents. The antifungal agents comprising these compounds as the effective ingredient are useful for the treatment of fungal diseases, including those affecting humans or other mammals, in which fungi or yeast participate. Oral or parenteral administration of the anti-fungal agent to human or mammalian patients can result in termination or inhibition of the growth of fungi. Conventional preparations, such as tablets, capsules or elixirs are suitable in the case of oral administration; and in the case of parenteral administration, conventional sterile solutions or suspensions are suitable. Where the compounds of the present invention are used as the effective ingredient, the compounds may be administered to the patient (animal or human) requiring such treatment in a dose range of 10 to 1000 mg per patient. The dose may vary depending upon the severity of the disease, body weight of the patient and/or other factors known to one skilled in the art.

The compounds may be used in the form of physiologically acceptable salts or mixtures thereof, and may be mixed with each other in a unit dose form generally recognized in the art, required for preparing pharmaceutical preparations, together with a physiologically acceptable vehicle, carrier, excipient, binder, preservative, stabilizer, flavoring agent, etc. The amount of the active substance in such compositions or preparations corresponds to an amount which yields a suitable dose as indicated above.

Specific examples of chemicals which may be mixed with the active substance to prepare tablets, capsules, etc., include the following compounds: binders such as gum arabic, corn starch or gelatin; excipients such as microcrystalline cellulose; swelling agents such as alginic acid, etc.; lubricants such as magnesium stearate, etc.; dissolution aids such as sodium deoxycholate, etc.; sweeteners such as sucrose, lactose, etc.; flavoring agents such as peppermint, etc.; and in the case of capsules (preparation in unit form), further liquid carriers such as oils and fats, in addition to the compounds described above.

Various other materials may be present as coating agents, or for the purpose of changing the physical shape of the preparation unit. For example, tablets may be coated with Shellac or sucrose or both. Syrups or elixirs may contain the active compound, sucrose as a sweetener, methyl and propyl parabens as preservatives, pigments and flavors such as cherry or orange flavor, in addition to a conventional syrup or elixir base (for example, water, ethanol, mixtures thereof, etc.).

Sterile compositions for injection may be formulated in a conventional manner for preparing pharmaceutical compositions, which comprises dissolving or suspending the active substance in a vehicle such as water or saline for injection, in natural vegetable oil such as sesame oil, palm oil, peanut oil, cotton seed oil, etc., or in a synthetic fat vehicle such as ethyl oleate, etc. A buffer, a preservative, an antioxidant, etc., may also be incorporated, if necessary and/or if desired.

Other features of the invention will become apparent in the course of the following descriptions of exemplary embodiments which are given for illustration of the invention, and are not intended to be limiting thereof.

EXAMPLES (1) Preparation of AJI9463A, AJI9463B and AJI9463C

A medium, pH 7.2, composed of 1.5 g of glucose, 0.5 g of meat extract, 0.2 g of peptone, 0.1 g of yeast extract and 100 ml of water was prepared and placed in a 500 ml Sakaguchi flask. After sterilization at 120° C. for 20 minutes, one platinum loop of slant culture cake of *Streptomyces sp.* AJ9463 (FERM BP-2801) was inoculated into the medium, and was shake cultured at 28° C. for 3 days to obtain a primary seed mother liquor.

In a second procedure, 3 liters of a medium having the same composition as above was prepared. Separately, each of three 5-L Sakaguchi flasks were charged with 1 liter of the resulting medium, and the flasks and their contents were sterilized at 120° C. for 30 minutes. Each flask was then charged with 20 ml of the primary seed mother liquor described above. The flask was shaken at 28° C. for 3 days to obtain a secondary seed mother liquor.

In a third procedure, 150 liters of medium having the same composition as above were prepared and placed in a culture tank. The tank and its contents were sterilized at 120° C. for 30 minutes. The tank was charged with 3 liters of the secondary seed mother liquor described above, and was shake cultured at 27° C. for 66 hours. At this stage, the stirring velocity was 200 rpm and the aerial rate was 38 l/min. The resulting culture broth was centrifuged by a sharpless centrifuging machine to recover the cells. The wet weight of the centrifuged cells was 2.6 kg.

To the cells was added 15 liters of methanol. Extraction was conducted overnight. Celite was added to the extract, and filtration was performed through a funnel to separate the cells from the extract. Subsequently, 8 liters of 80% methanol was added to the cells, and extraction was conducted for 3 hours. The cells were separated from the extract through a funnel. The resulting extracts were combined and concentrated under reduced pressure. After methanol was removed, sufficient distilled water was added to make a total volume of 6 liters.

The resulting aqueous solution was adsorbed onto a $\phi 5.5 \times 49$ cm column packed with activated carbon. After washing with 2 liters of distilled water, the column was eluted successively with 5 liters of 10% ethanol, 5 liters of 25% ethanol, 5 liters of 50% ethanol, and 50% ethanol having a pH adjusted to 3.5 with acetic acid. The fraction eluted with 50% ethanol was combined with the fraction eluted with 50% ethanol of pH 3.5. The mixture was concentrated under reduced pressure to remove ethanol. Sufficient distilled water was added to the concentrate to make a total volume of 5 liters. At this stage, the pH of the solution was 3.45.

The solution was passed through an SP-Sephadex C-25 (manufactured by Pharmacia Fine Chemicals, Inc.) column of $\phi 2 \times 54$ cm, equilibrated with 50 mM ammonium acetate (pH 5.0), then eluted with 50 mM ammonium acetate (pH 5.0). The active fraction was recovered and lyophilized.

The lyophilized product was dissolved in 30 ml of 0.1N acetic acid, and then purified by high performance liquid chromatography using Capcell Pak ODS Column (Capcell Pak $C_{18}$ SG120 column; $\phi 20 \times 250$ mm, 5 $\mu$m packing agent particle diameter, manufactured by SHISEIDO Co., Ltd.) in 500 $\mu$fractions. Elution was performed using a linear gradient of aqueous ammonium acetate:acetonitrile, wherein 10 mM aqueous ammonium acetate (pH 8.9) was used for the initial 2 minutes, and thereafter, the acetonitrile concentration was linearly increased to a final concentration of 40%. The flow rate was 5 ml/min. Each active component was detected by UV absorption at 220 nm. The elution times for known components under the elution conditions described above were 28.0 minutes for demethylallosamidin; 37.6 minutes for allosamidin; and 41.2 minutes for methylallosamidin. For the present compounds, elution times were 32.5 minutes, 31.2 minutes and 39.1 minutes, respectively, for AJI9463A, AJI9463B and AJI9463C.

Each component was fractionated and concentrated under reduced pressure. Each concentrate was then lyophilized. The yields of AJI9463A, AJI9463B and AJI9463C were 0.4 mg, 1.2 mg and 2.1 mg, respectively.

(2) Preparation of AJI9463A, AJI9463B and AJI9463C

A medium, pH 7.2, composed of 1.5 g of glucose, 0.5 g of meat extract, 0.2 g of peptone, 0.1 g of yeast extract and 100 ml of water was prepared and placed in a 500 ml Sakaguchi flask. After sterilization at 120° C. for 20 minutes, one platinum loop of slant culture cake of *Streptomyces sp.* AJ9472 (FERM BP-3705) was inoculated into the medium, and was shake cultured at 28° C. for 3 days to obtain a primary seed mother liquor.

In a second procedure, 4 liters of a medium having the same composition as above was prepared. Separately, each of four 5-L Sakaguchi flasks were charged with 1 liter of the resulting medium, and the flasks and their contents were sterilized at 120° C. for 30 minutes. Each flask was then charged with 20 ml of the primary seed mother liquor described above. The flask was shaken at 28° C. for 3 days to obtain a secondary seed mother liquor.

In a third procedure, 200 liters of medium having the same composition as above were prepared and placed in a culture tank. The tank and its contents were sterilized at 120° C. for 30 minutes. The tank was charged with 4 liters of the secondary seed mother liquor described above, and was shake cultured at 27° C. for 66 hours. At this stage, the stirring velocity was 200 rpm and the aerial rate was 50 l/min. The resulting culture broth was centrifuged by a sharpless centrifuging machine to recover the cells. The wet weight of the centrifuged cells was 4.5 kg.

To the cells was added 20 liters of methanol. Extraction was conducted overnight. Celite was added to the extract, and filtration was performed through a funnel to separate the cells from the extract. Subsequently, 8 liters of 80% methanol was added to the cells, and extraction was conducted for 3 hours. The cells were separated from the extract through a funnel. The resulting extracts were combined and concentrated under reduced pressure. After methanol was removed, sufficient distilled water was added to make a total volume of 8 liters.

The resulting aqueous solution was adsorbed onto a $\phi 6 \times 50$ cm column packed with activated carbon. After washing with 2.4 liters of distilled water, the column was eluted successively with 7 liters of 10% ethanol, 7 liters of 25% ethanol, 7 liters of 50% ethanol, and 50% ethanol having a pH adjusted to 3.5 with acetic acid. The fraction eluted with 50% ethanol was combined with the fraction eluted with 50% ethanol of pH 3.5. The mixture was concentrated under reduced pressure to remove ethanol. Sufficient distilled water was added to the concentrate to make a total volume of 7 liters. At this stage, the pH of the solution was 3.45.

The solution was passed through an SP-Sephadex C-25 (manufactured by Pharmacia Fine Chemicals, Inc.) column of $\phi 2.4 \times 60$ cm, equilibrated with 50 mM ammonium acetate (pH 5.0), then eluted with 50 mM ammonium acetate (pH 5.0). The active fraction was recovered and lyophilized.

The lyophilized product was dissolved in 40 ml of 0.1N acetic acid, and then purified by high performance liquid chromatography using Capcell Pak ODS Column (Capcell Pak $C_{18}$ SG120 column; $\phi 20 \times 250$ mm, 5 $\mu$m packing agent particle diameter, manufactured by SHISEIDO Co., Ltd.) in 500 $\mu$l fractions. Elution was performed using a linear gradient of aqueous ammonium acetate:acetonitrile, wherein 10 mM aqueous ammonium acetate (pH 8.9) was used for the initial 2 minutes, and thereafter, the acetonitrile concentration was linearly increased to a final concentration of 40%. The flow rate was 5 ml/min. Each active component was detected by UV absorption at 220 nm. The elution times for known components under the elution conditions described above were 28.0 minutes for demethylallosamidin; 37.6 minutes for allosamidin; and 41.2 minutes for methylallosamidin. For the present compounds, elution times were 32.6 minutes, 31.2 minutes and 39.1 minutes, respectively, for AJI9463A, AJI9463B and AJI9463C.

Each component was fractionated and concentrated under reduced pressure. Each concentrate was then lyophilized. The yields of AJI9463A, AJI9463B and AJI9463C were 10.7 mg, 70.6 mg and 121.3 mg, respectively.

(3) Preparation of partially hydrolyzed disaccharides of AJI9463A, AJI9463B and AJI9463C In this example, hydrolysis of AJI9463C is recited, but the other partially hydrolyzed disaccharides can be prepared by an identical procedure.

A 20 eggplant flask was charged with AJI9463C (12.6 mg) and dissolved in 3 ml of 0.5N hydrochloric acid. After sealing, the flask was heated at 70° C. for 390 minutes on an oil bath. The reaction solution was purified by high performance liquid chromatography using the Capcell Pak ODS column shown in Example (1) described above. The conditions for elution were the same as those described in Example (1) above. The elution time of the partially hydrolyzed disaccharide of AJI9463C was 32.8 minutes under the HPLC conditions described.

Figure 4:
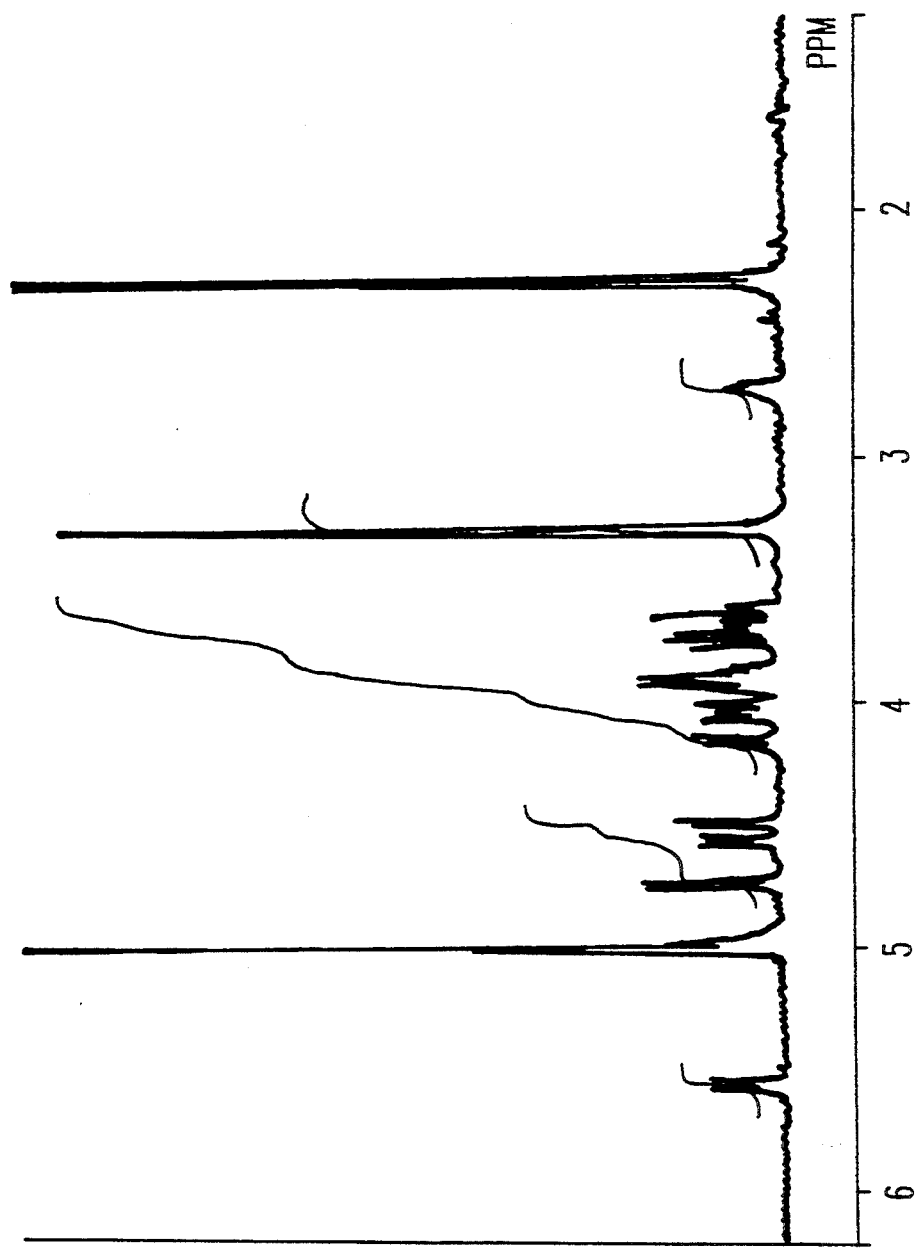
FIG. 4 shows the proton nuclear magnetic resonance spectrum of the partially hydrolyzed disaccharide of AJI9463C.

The resulting partially hydrolyzed disaccharide of AJI9463C (corresponding to the compound having chemical structural formula (2), wherein $R_1$ is methyl, $R_2$ is hydroxy and $R_3$ is hydrogen) has the following physicochemical properties:

(a) External appearance: white powder
(b) Molecular weight: 419 (FAB MS: m/z 420 $(M+H)^+$, glycerol matrix)
(c) Molecular formula: $C_{17}H_{29}N_3O_9$
(d) UV absorption spectrum: terminal absorption in 0.1 N acetic acid
(e) $^1$H-nuclear magnetic resonance spectrum (400 MHz, $D_2O$ containing 0.5% $CD_3CO_2H$): see FIG. 4

(4) Assay for chitinase inhibitory activity by AJI9463A, AJI9463B, AJI9463C, and the partially hydrolyzed disaccharides thereof (i) Preparation of chitinase solution The chitinase from *Candida albicans* (*C. albicans*) was prepared by the following method. Firstly, a Sabouraud medium (pH 5.6) composed of 4 g of glucose, 1 g of polypeptone and 100 ml of water was prepared and placed in an Erlenmeyer flask of 500 ml volume. After sterilization at 120° C. for 20 minutes, one platinum loop of slant culture cells of *C. albicans* ATCC 10231 was inoculated into the medium, and then shake cultured at 37° C. for 2 days to obtain a primary seed mother liquor.

In a second procedure, 1 liter of Sabouraud medium having the same composition as above was prepared. Separately, 100 ml of the medium was added to each of ten 500 ml Erlenmeyer flasks, then the flasks and their contents were sterilized at 120° C. for 20 minutes. Thereafter, 2 ml of the primary seed mother liquor described above was added to each flask. The flask was shaken at 37° C. for 2 days to obtain a secondary seed mother liquor.

In a third procedure, 50 liters of Sabouraud medium having the same composition as described above was prepared and added to a culture tank of 100 liter volume. The tank and its contents were sterilized at 120° C. for 30 minutes. In the tank, 1 liter of the secondary seed mother liquor described above was added. Shake culturing was then conducted at 37° C. for 15 hours. At this stage, the stirring velocity was 140 rpm and the aerial rate was 10 l/min. The resulting culture broth was centrifuged by a sharpless centrifuging machine to recover the cells. The wet weight of the thus obtained cells was 250 g.

The cells were suspended in 800 ml of a buffer for cell homogenization (50 mM bis-Tris, 0.25M saccharose, 1 mM disodium ethylenediaminetetraacetate, pH 6.5). The suspension was twice passed through a Dyno-mill disintegrator (beads: MK-2GX, 0.25–0.5 mm) to disrupt the cells, and the supernatant was recovered. The supernatant was centrifuged at 9000 g for 30 minutes, then further super-centrifuged at 152,000 g for an hour. The supernatant thereof was recovered, and was concentrated to about one-fifth of the volume by ultrafiltration (Toyo Ultrafilter UP-20), having an excluding limiting molecular weight of 20,000. The concentrate was used as the crude chitinase solution from *Candida albicans* in the assay described in procedure (ii) below.

The chitinase from baker's yeast (*S cerevisiae*) was prepared by the following method. Firstly, 400 g of baker's yeast (manufactured by Kanegafuchi Chemical Industry Co., Ltd.) was suspended in buffer for enzyme extraction (0.1% digitonin: manufactured by Wako Pure Chemical Industry Co., Ltd.), 0.1% β-mercaptoethanol and 2 liters of 25 mM MES (manufactured by Nakarai Chemical Co., Ltd.), and was shaken at 30° C. for 2 hours at 120 spm to extract the enzyme. The extract was centrifuged at 12,000 g for 10 minutes and the supernatant was recovered. The supernatant was concentrated to about one-fifth of the volume by ultrafiltration (UP-20). After 800 ml of sodium citrate buffer (obtained by adding 0.15M aqueous sodium citrate to 0.15M aqueous citric acid, and adjusting the pH to 3.0) was added to the concentrate, the precipitates were removed by centrifugation (0° C., 12,000 g, 10 minutes). The supernatant was again concentrated by ultrafiltration (UP-20) to about 80 ml. The resulting concentrate was used as the chitinase from baker's yeast in the assay described in procedure (ii) below.

The chitinase from *Trichoderma sp.* was provided for use in the assay described in procedure (ii) below by diluting commercially available Chitinase T-1 (manufactured by Asahi Industry Co., Ltd.) with McIlvanine buffer (obtained by adding 0.2M aqueous disodium hydrogen phosphate to 0.1M aqueous citric acid and adjusting the pH to 5.2) to a concentration of 50 μg/ml.

(ii) Assay for chitinase inhibitory activity

In a 20 ml vial bottle, 50 μl of the chitinase solution from *Candida albicans* prepared as described above, s 50 μl of 100 μg/ml aqueous 4-methylumbelliferyl β-D-N,N',N"-triacetyl-chitotrioside (hereinafter abbreviated as 4MBTC, SIGMA Co.), 75 μl of 50 mM bis-Tris buffer (pH 6.5) and 25 μl of 0.1N acetic acid were added and mixed. The reaction was carried out at 37° C. for 30 minutes. As a blank, the reaction was carried out in an identical manner, substituting 50 mM bis-Tris buffer (pH 6.5) for the enzyme solution. After the reaction, sufficient 0.5M glycine-sodium hydroxide buffer (pH 10.4) was added to make the total volume 5 ml. Then, the fluorescent intensity was determined with a fluorophotometer (manufactured by Hitachi Ltd., MPF-4). The excited wavelength was 350 nm, and the fluorescent wavelength was 400 nm. Chitinase activity was determined using the difference in the fluorescent intensity between the read-out data from the sample containing the enzyme and the blank read-out data.

In determining the inhibitory activity of AJI9463A, AJI9463B, AJI9463C, and the partially hydrolyzed disaccharides thereof, each compound was dissolved in 0.1N acetic acid, and 25 μl of the compound solution was substituted for the 25 μl of 0.1N acetic acid in the reaction system described above. Further, in determining the inhibitory activity against the chitinases of baker's yeast and *Trichoderma sp.*, the assay was performed by changing the buffer in the reaction system described above from 50 mM bis-Tris buffer (pH 6.5) to 0.1M citrate buffer (pH 3.0) and McIlvanine buffer (pH 5.2), respectively.

(iii) Results

The enzyme inhibitory activities ($IC_{50}$, reported in μg/ml) of AJI9463A, AJI9463B, AJI9463C, and the partially hydrolyzed disaccharides thereof against the chitinases from *Candida albicans*, baker's yeast and *Trichoderma sp.* are shown in Table 1 below.

TABLE 1

| Compound | Chitinase Inhibitory Activity $IC_{50}$ (μg/ml) | | |
|---|---|---|---|
| | C. albicans | S. cerevisiae | Trichoderma sp. |
| AJI9463A | 0.6 | 0.4 | 1.3 |
| AJI9463B | 0.8 | 0.5 | 1.6 |
| AJI9463C | 3.4 | 31.3 | 0.8 |
| Partially hydrolyzed disaccharide of AJI9453A | 0.9 | >200.0 | >50.0 |
| Partially hydrolyzed disaccharide of AJI9463B | 1.0 | >200.0 | >50.0 |
| Partially hydrolyzed disaccharide of AJI9463C | 1.3 | >200.0 | >50.0 |
| Allosamidin | 6.2 | 33.8 | 0.8 |
| Methylallosamidin | 8.8 | 37.2 | 1.2 |

(5) Effects of AJI9463A, AJI9463B and AJI9463C and the partially hydrolyzed disaccharides thereof on growth of *Candida albicans*

Samples of *Candida albicans* (ATCC 10231) were precultured in Sabouraud dextrose medium. Each of seven large test tubes containing 5 ml of Sabouraud dextrose medium were charged, respectively, with 50 μg/ml of AJI9463A, AJI9463B, AJI9463C, and the partially hydrolyzed disaccharides thereof and medium containing no active inhibitory component. The preculture was then inoculated into the media in the test tubes. The test tubes were capped with a cotton stopper, and incubated at 37° C. at 120 spm. The change in the subsequent culture with respect to time was observed. Observations were made microscopically, sampling the medium at the time when the culture started, and 6 and 9 hours thereafter.

Fungal growth generally was somewhat inhibited 6 and 9 hours after inoculation in the test tubes containing AJI9463A, AJI9463B, AJI9463C and the partially hydrolyzed disaccharides thereof. However, the fungal count in one group was clearly increased, and a morphological abnormality (inhibition of the cell fission after budding) was observed. This morphological abnormality was especially apparent 6 hours after the start of culture.

(6) Cytotoxicity of AJI9463A, AJI9463B, AJI9463C and the partially hydrolyzed disaccharides thereof Six separate samples of mouse ascites breast cancer cells FM3A, inoculated in Dulbeccol's modified MEM medium supplemented with 10% calf fetal serum ($1 \times 10^5$ counts/ml) were prepared, and AJI9463A, AJI9463B, AJI9463C and each of the partially hydrolyzed disaccharides thereof were respectively added thereto, resulting in a concentration of 1 mg/ml. Stationary culture was conducted at 37° C. for 4 days. The cultured mouse ascites breast cancer cells FM3A were observed microscopically. No growth inhibition was noted at all.

Six separate samples of human leukemia cells K562, inoculated in RPMI 1640 medium supplemented with 10% calf fetal serum ($1 \times 10^5$ counts/ml) were prepared, and AJI9463A, AJI9463B, AJI9463C and each of the partially hydrolyzed disaccharides thereof were respectively added thereto, resulting in a concentration of 1 mg/ml. Stationary culture was conducted at 37° C. for 4 days. The human leukemia cell K562 culture was observed microscopically. No growth inhibition was noted at all.

The novel allosamidin compounds of the present invention, AJI9463A, AJI9463B and AJI9463C, exhibit an extremely potent inhibitory activity against the chitinase derived from pathogenic fungi *Candida albicans*, as well as the chitinases from baker's yeast and *Trichoderma sp.* Therefore, the present invention provides useful, broad-spectrum chitinase inhibitors and antifungal agents having excellent effects. These compounds are produced by fermentation, and thus, are readily mass-produced.

On the other hand, the compounds of chemical structure (2) have low molecular weights but exhibit extremely potent inhibitory activity against the chitinase from *Candida albicans*. Furthermore, AJI9463B and AJI9463C are advantageous for mass production by chemical synthesis, since these compounds have as the constituent component N-acetyl-glucosamine, a starting material naturally present in large quantities. Therefore, the present invention provides antifungal agents and chitinase inhibitors having excellent effects which are readily mass-produced industrially.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A compound represented by the following chemical structure (2):

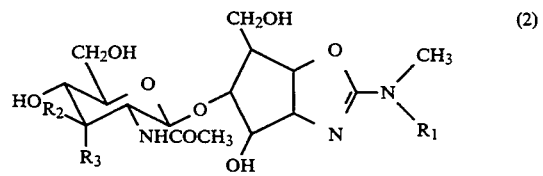

wherein $R_1$ and $R_2$ are hydrogen and $R_3$ is hydroxy; $R_1$ and $R_3$ are hydrogen and $R_2$ is hydroxy; or $R_1$ is methyl, $R_2$ is hydroxy and $R_3$ is hydrogen.

2. The compound of claim 1, wherein $R_1$ and $R_2$ are hydrogen and $R_3$ is hydroxy.

3. The compound of claim 1, wherein $R_1$ and $R_3$ are hydrogen and $R_2$ is hydroxy.

4. The compound of claim 1, wherein $R_1$ is methyl, $R_2$ is hydroxy and $R_3$ is hydrogen.

5. A composition comprising an amount of a compound effective for the inhibition of the growth of a fungus, said compound having the chemical structure (2):

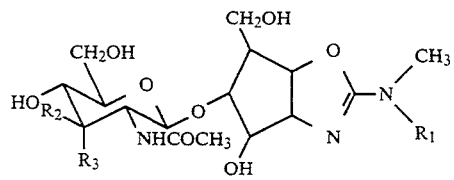
(2)

wherein $R_1$ and $R_2$ are hydrogen and $R_3$ is hydroxy; $R_1$ and $R_3$ are hydrogen and $R_2$ is hydroxy; or $R_1$ is methyl, $R_2$ is hydroxy and $R_3$ is hydrogen, in an inert carrier.

6. The composition of claim 5, wherein said compound is the compound of chemical structure (2), $R_1$ and $R_2$ are hydrogen and $R_3$ is hydroxy.

7. The composition of claims 5, wherein said compound is the compound of chemical structure (2), $R_1$ and $R_3$ are hydrogen and $R_2$ is hydroxy.

8. The composition of claim 5, wherein said compound is the compound of chemical structure (2), $R_1$ is methyl, $R_2$ is hydroxy and $R_3$ is hydrogen.

* * * * *

UNITED STATES PATENT AND TRADEMARK OFFICE
CERTIFICATE OF CORRECTION

PATENT NO.   : 5,413,991
DATED        : May 9, 1995
INVENTOR(S)  : Yasuhiro YAMADA, et al.

It is certified that error appears in the above-indentified patent and that said Letters Patent is hereby corrected as shown below:

On the title page, Item [75], the third inventor's city of residence should read:

--Kawasaki--

Signed and Sealed this

Fourth Day of July, 1995

Attest:

BRUCE LEHMAN

Attesting Officer

Commissioner of Patents and Trademarks